US012758339B2

(12) United States Patent
Mueller et al.

(10) Patent No.: US 12,758,339 B2
(45) Date of Patent: Oct. 13, 2026

(54) FORCE TRANSMISSION SYSTEMS USING PLANETARY GEAR ASSEMBLY, AND RELATED DEVICES AND METHODS

(71) Applicant: INTUITIVE SURGICAL OPERATIONS, INC., Sunnyvale, CA (US)

(72) Inventors: Liliann Mueller, New Haven, CT (US); Ronald G. Litke, Sandy Hook, CT (US); Adam J. Ross, Prospect, CT (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 232 days.

(21) Appl. No.: 18/702,489

(22) PCT Filed: Oct. 18, 2022

(86) PCT No.: PCT/US2022/046979
§ 371 (c)(1),
(2) Date: Apr. 18, 2024

(87) PCT Pub. No.: WO2023/069404
PCT Pub. Date: Apr. 27, 2023

(65) Prior Publication Data

US 2024/0415591 A1 Dec. 19, 2024

Related U.S. Application Data

(60) Provisional application No. 63/257,185, filed on Oct. 19, 2021.

(51) Int. Cl.
*F16H 25/20* (2006.01)
*A61B 34/37* (2016.01)
(Continued)

(52) U.S. Cl.
CPC ............ *A61B 34/37* (2016.02); *F16H 13/06* (2013.01); *A61B 2017/00327* (2013.01); *F16H 2025/2059* (2013.01)

(58) Field of Classification Search
CPC ..... F16H 2025/2053; F16H 2025/2059; F16H 1/227; F16H 2025/2481; F16H 19/02;
(Continued)

(56) References Cited

U.S. PATENT DOCUMENTS

| | | | |
|---|---|---|---|
| 8,151,661 B2 | 4/2012 | Schena et al. | |
| 8,852,208 B2 | 10/2014 | Gomez et al. | |

(Continued)

FOREIGN PATENT DOCUMENTS

| | | | |
|---|---|---|---|
| DE | 20115608 U1 * | 2/2003 | F16H 25/20 |
| EP | 0301960 B1 * | 11/1991 | F16H 25/20 |
| JP | 2016530956 A | 10/2016 | |

OTHER PUBLICATIONS

International Search Report and Written Opinion for Application No. PCT/US2022/046979, mailed Mar. 23, 2023, 16 pages.

(Continued)

*Primary Examiner* — Sherry L Estremsky
(74) *Attorney, Agent, or Firm* — Jones Burke, PLLC

(57) ABSTRACT

An instrument includes a shaft, a moveable component coupled to the shaft, and an actuation member drive assembly coupled to the shaft. The actuation member drive assembly may include a rotatable drive member, a ring gear operably coupled to the rotatable drive member and configured to rotate in response to rotation of the rotatable drive member, and a planet gear meshed with the ring gear. The instrument further includes an actuation member extending through the shaft and operably coupled to the moveable component and the planet gear. The actuation member is moveable in translation in response to rotation of the planet (Continued)

gear. Devices and methods relate to actuation member drive assemblies.

18 Claims, 12 Drawing Sheets

(51) Int. Cl.
*F16H 13/06* (2006.01)
*A61B 17/00* (2006.01)

(58) Field of Classification Search
CPC .................. F16H 37/124; F16H 25/20; F16H 2025/2087; F16H 2025/204; A61B 2017/00327
USPC ........................................................ 74/89.28
See application file for complete search history.

(56) References Cited

U.S. PATENT DOCUMENTS

| | | | | |
|---|---|---|---|---|
| 8,968,312 | B2 * | 3/2015 | Marczyk | A61B 17/29 606/51 |
| 9,055,961 | B2 | 6/2015 | Manzo et al. | |
| 9,295,524 | B2 | 3/2016 | Schena et al. | |
| 9,358,074 | B2 | 6/2016 | Schena et al. | |
| 10,470,830 | B2 | 11/2019 | Hill et al. | |
| 10,568,640 | B2 * | 2/2020 | Bozung | A61B 17/1617 |
| 10,710,246 | B2 | 7/2020 | McGrogan et al. | |
| 10,945,797 | B2 * | 3/2021 | Anglese | A61B 34/30 |
| 11,320,031 | B2 * | 5/2022 | Crawford | B23Q 5/326 |
| 11,419,691 | B2 * | 8/2022 | Kim | A61B 34/74 |
| 11,624,429 | B1 * | 4/2023 | Hopkins | F16H 37/124 74/89.28 |
| 11,751,954 | B2 * | 9/2023 | Beckman | F16H 25/20 606/1 |
| 2013/0334281 | A1 | 12/2013 | Williams | |
| 2019/0231330 | A1 | 8/2019 | Xu et al. | |
| 2019/0239877 | A1 | 8/2019 | Ragosta et al. | |
| 2019/0239967 | A1 | 8/2019 | Ragosta et al. | |
| 2020/0237423 | A1 | 7/2020 | Witte et al. | |

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

FORCE TRANSMISSION SYSTEMS USING PLANETARY GEAR ASSEMBLY, AND RELATED DEVICES AND METHODS

CROSS-REFERENCE TO RELATED APPLICATION

This application is a U.S. national stage application under 35 U.S.C. § 371(c) of International PCT Application No. PCT/US2022/046979, filed Oct. 18, 2022, which claims the benefit of priority to U.S. Provisional Application No. 63/257,185, filed Oct. 19, 2021 and titled "FORCE TRANSMISSION SYSTEMS USING PLANETARY GEAR ASSEMBLY, AND RELATED DEVICES AND METHODS" the entire contents of each of which are incorporated by reference herein.

TECHNICAL FIELD

Aspects of the present disclosure relate to force transmission systems and related devices and methods. For example, aspects of the present disclosure relate to force transmission systems that convert rotational input forces to translational forces that can be transmitted along an instrument to actuate components of the instrument.

INTRODUCTION

Various tools such as medical (including surgical) or industrial instruments often include shafts having one or more components that impart one or more degrees of freedom of movement to such instruments. Such components can be in the form of end effectors that move in one or more degrees of freedom, such as for example, translating mechanisms, jaws that open and close, etc. Other such components may include articulable structures, such as joint mechanisms along the shaft that are pivotable (e.g., in pitch and/or yaw) relative to the shaft. These articulable structures can be actuated and controlled via translating actuation members extending along a length of the shaft. Such actuation members may include, for example, tension members, such as cables, wires, or the like, or compression members, such as rods. These actuation members extend through the instrument shaft to couple to the actuatable component and a drive member at a force transmission system at a proximal portion of the instrument shaft. In this way, the actuation members transmit forces from the force transmission system to the actuatable component. Force transmission systems can have manually-operated inputs for instruments that are manually operated or can include input interfaces that are configured to engage with a manipulator system of a teleoperated, computer-assisted system, which manipulator systems comprise motorized output drives that are under control from remote input mechanisms, as would be familiar to those of ordinary skill in the art.

In some force transmission systems, the drive members to which tension-type actuation members are coupled are rotary drive members, such as capstans, driven by a drive shaft. Rotary motion causes the tension actuation members to be paid in and paid out to transmit force to the actuatable component. Moreover, depending on the arrangement of the force transmission system, the actuation members may be required to follow relatively complex paths to their coupling with the drive member, such as being routed around one or more pulleys or other routing mechanisms to a drive member of the force transmission system. These mechanisms may limit the possible types of actuation members that can be used to tension-type actuation members, such as cables, wires, other filament structures, or the like, that are relatively flexible in multiple degrees of freedom. In addition, with tension actuation members, rotation (or roll) of an instrument shaft can produce twisting of multiple tension actuation members within the force transmission system, which can in turn produce undesirable friction when attempting to actuate those actuation members.

In addition, to reduce backlash and facilitate accurate movement and control of the articulable components, particularly articulable structures for example, it is sometimes desired to pre-tension the actuation members during manufacturing of the instrument to remove slack that would otherwise lead to inaccuracies in movement and positioning articulable of the actuatable component. Such pre-tensioning can introduce additional complexity to the manufacturing process, particularly with instruments that include directional changes of the actuation members, e.g., around pulleys, capstans, or other routing mechanisms within the force transmission system, as discussed above. In such arrangements, pre-tensioning cannot occur until the cables are routed through the various devices at the force transmission system, which poses a challenge for removing the shaft and end effector portion of the instrument from the force transmission system without disassembling the various actuation members from the components of the force transmission system.

Additionally, in some instruments, such articulation members are in the form of tendons extending through tubes (e.g., coil pipes, hypotubes, or other types of tubing) that extend from the force transmission system and through the instrument shaft. Roll of the shaft (i.e., relative to the force transmission mechanism) can cause the coil pipes to wrap around the shaft (e.g., within an annular space of the shaft between internal and external shaft portions) and may place undesired tension on the coil pipes and/or limit the total rotational freedom of the shaft, in addition to causing excess friction and wear.

Further, the use of multiple actuation members to control multiple degrees of freedom of one or more actuatable components can further complicate manufacture of the instruments. In particular, the routing and operable coupling of multiple actuation members poses challenges in attempting to automate manufacturing of the instruments due to the many routing paths and connections that may be needed.

There exists a need for force transmission systems that simplify and facilitate manufacturing, and that provide robust and reliable force transmission for the actuation of actuatable components of instruments and fewer constraints on a roll degree of freedom of the shaft. In particular, there exists a need to provide force transmission systems and their corresponding actuation members that may enable more automated manufacturing of instruments, as well as the potential to modularize the ability of an instrument force transmission system to interface with various drive inputs. Moreover, a need exists to simplify and provide greater flexibility in the pre-tensioning of the actuation members of instruments.

SUMMARY

Embodiments of the present disclosure may solve one or more of the above-mentioned problems and/or may demonstrate one or more of the above-mentioned desirable features. Other features and/or advantages may become apparent from the description that follows.

In accordance with at least one aspect of the present disclosure, an instrument includes a shaft, a moveable component coupled to the shaft, and an actuation member drive assembly coupled to the shaft. The actuation member drive assembly may include a rotatable drive member, a ring gear operably coupled to the rotatable drive member and configured to rotate in response to rotation of the rotatable drive member, and a planet gear meshed with the ring gear. The instrument further includes an actuation member extending through the shaft and operably coupled to the moveable component and the planet gear. The actuation member is moveable in translation in response to rotation of the planet gear. Devices and methods relate to actuation member drive assemblies.

In another aspect of the present disclosure, an instrument comprises a shaft, an articulable component coupled to the shaft and configured to articulate relative to the shaft, and a force transmission system coupled to the shaft. The force transmission system comprises a ring gear, a first planet gear meshed with the ring gear, a second planet gear meshed with the ring gear, a first lead screw comprising left-hand screw threading in threaded engagement with the first planet gear, and a second lead screw comprising right-hand screw threading in threaded engagement with the second planet gear. The instrument further comprises a first actuation member extending through the shaft and operably coupled to the articulable component and the first lead screw; and a second actuation member extending through the shaft and operably coupled to the articulable component and the second lead screw.

In yet another aspect of the present disclosure, a method of tensioning first and second actuation members coupled to an articulable structure of a medical instrument. The method comprises applying a first tensile force to a first actuation member coupled to a first lead screw by driving the first lead screw, applying a second tensile force to a second actuation member coupled to a second lead screw by driving the second lead screw, maintaining the first tensile force in the first actuation member by coupling the first lead screw with a first planet gear and meshing the first planet gear to a ring gear, and maintaining the second tensile force in the second actuation member by engaging the second lead screw with a second planet gear and meshing the second planet gear to the ring gear.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are for example and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure and are incorporated in and constitute a part of this specification. The drawings illustrate one or more embodiments of the present teachings and together with the description explain certain principles and operation. In the drawings.

DETAILED DESCRIPTION

Figure 1:
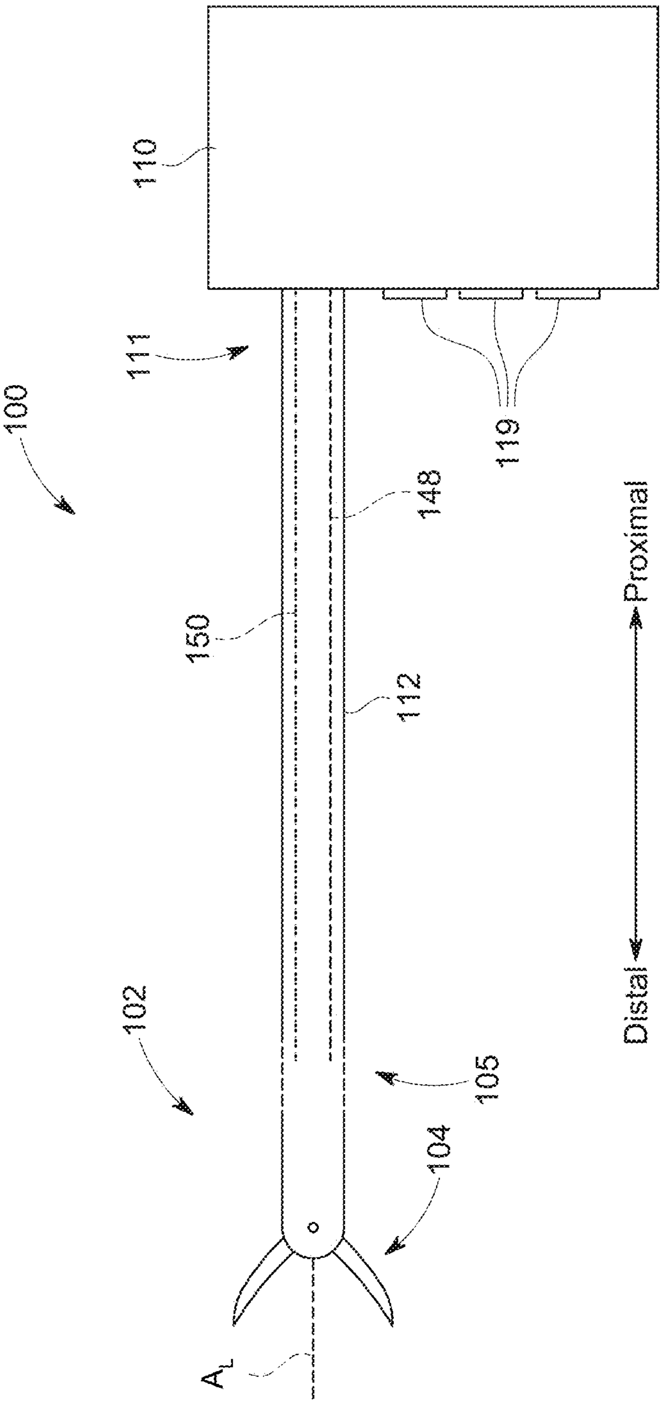
FIG. 1 is a schematic, side view of an embodiment of an instrument comprising a force transmission system according to various embodiments of the present disclosure.

Embodiments of the present disclosure relate to instruments and associated force transmission systems that are configured to drive actuation of operatively couple actuation members that in turn transmit force to actuate actuatable components, such as for example articulable structures, coupled at more distal portions of the shafts of the instruments. In various embodiments, the force transmission systems are configured to further be operably coupled with drive systems of manipulators, such as computer-controlled (e.g., teleoperated) or manual (e.g., laparoscopic) manipulators. Force transmission systems and actuation member drive assemblies of those systems can, according to various embodiments facilitate manufacturability, e.g., by facilitating use of automated manufacturing processes. Moreover, they can provide for less complexity in operably coupling actuation members to the actuation member drive assemblies, such as for example, by reducing or eliminating the use of pulleys, capstans, and other drive and routing mechanisms found in drive assemblies that are configured for use with tendon actuation members. Additionally, instrument and associated force transmission system configurations as disclosed herein can promote modularity of instrument design, such as by enabling a drive assembly of the force transmission system to interface with various types of manipulator interfaces to provide drive forces to the force transmission system.

Various embodiments of the disclosure include an actuation member drive assembly configured to allow for relatively easy interface with other drive members, such as idler gears, belts, or other mechanical components of an overall force transmission system used to operate the instrument. The actuation member drive assembly can include components coupled to the actuation members in a manner that maintains a preload tension in the actuation members regardless of the actuation member drive assembly's engaged or non-engaged state with the other components of the force transmission system. Further, the preload tension experienced by the actuation members is not transmitted to other drive members of the force transmission system. Stated differently, the preload tension is isolated to the actuation members and the actuation member drive assembly and is not experienced by the other drive members of the force transmission system to which the actuation member drive assembly are engaged.

Various embodiments of the present disclosure can permit the instrument with the force transmission system to undergo maintenance servicing without releasing the tension in the actuation members, or for exchanging the shaft and sub-assembly between force transmission systems configured for different manipulators (e.g., between a manual, laparoscopic handle, and a force transmission system configured for use with a teleoperated surgical system).

Additionally, embodiments of the disclosure facilitate roll of the shaft by configuring the force transmission system such that the actuation members and associated actuation member drive system rotates with the shaft during roll, eliminating the cable wrap that can occur in other instrument configurations, e.g., in configurations in which the actuation members are in the form of coil pipes or other tubing extending through an annular space in the shaft.

Further, in instrument configurations in which the manipulator is relied on to tension the actuation members, embodiments of the disclosure contemplate the ability to maintain tensioning of the actuation members to a desired state regardless of whether external input forces are exerted on the drive members of the force transmission system. In this way a tension hold or lock state can occur so that the actuation members are tensioned to their desired degree and that tension is locked in place regardless of the instrument's connected or disconnected state with a manipulator. This may be particularly desirable in the case of instrument configured to be driven by a teleoperated manipulator system because removal of the instrument from the manipulator system will not result in a slack development in actuation members and loss of control of movement of the actuatable components operably coupled to the actuation members.

According to various embodiments of the disclosure, an actuation member drive assembly includes a ring gear engaged with two planet gears. Each of the planet gears is engageable with an associated actuation member via a lead screw engaged with a respective one of the planet gears (e.g., with internal threads within a bore of the planet gear). In some embodiments, the instrument includes one or more articulable structures along the shaft, each of the articulable structures having one or more degrees of freedom, and each degree of freedom is associated with one or more actuation members. For example, in an arrangement using pull-pull, tension actuation members, each degree of freedom of the articulable structure may be controlled by two pull-pull type actuation members.

In various exemplary embodiments, the articulable structure can have two degrees of freedom, for example, pitch and yaw. As discussed herein, the terms "pitch" and "yaw" refer to arbitrarily defined orthogonal directions and are used herein for simplicity of description. As such, each of the arbitrarily defined directions could be switched for one another without materially altering the substance of the disclosure. In such embodiments, the actuation member drive assembly can include multiple sets of ring and planet gears, each set being associated with a separate degree of freedom and independently actuatable to obtain the desired number of degrees of freedom.

In yet other embodiments of the disclosure, the actuation member drive assembly can be configured to rotate in a roll degree of freedom with the shaft. For example, in embodiments in which the instrument manipulator is operated with computer assistance (e.g., teleoperated), the controller can be configured to rotate the ring and planet gears to maintain a given pitch and yaw arrangement (in the frame of reference of the shaft) as the shaft rotates. Such an arrangement can be provided via a controller and associated software of the instrument manipulator.

Various embodiments also simplify actuation member routing and tensioning during manufacturing. As compared to other arrangements in which actuation members are routed through the shaft and the force transmission system to capstans or pulleys, and in which the actuation members follow a relatively complex path through the overall force transmission system of the instrument to operably couple with the drive members, embodiments disclosed herein can facilitate automation of manufacturing processes including assembly and tensioning of the actuation members, as discussed further herein.

Referring now to FIG. 1, a schematic, side view of an instrument 100 according to some embodiments of the disclosure is shown. Instrument 100 can be or include an instrument used to perform medical (e.g., surgical, diagnostic, and/or therapeutic) or non-medical procedures (e.g., industrial inspection applications). The instrument 100 includes an end effector 104, a shaft 112 elongated along a longitudinal axis $A_L$, between proximal end portion 111 and distal end portion 102 and a force transmission system 110. The end effector 104 is located at the distal end portion 102 of the shaft 112 and is configured to carry out a medical or non-medical (such as industrial) procedure. For example, the end effector 104 can include one or more tools such as gripping tools, staplers, shears, ligation clip appliers, electrosurgical tools, ultrasonic tools, suturing tools, or other types of tools. While the illustration of FIG. 1 depicts an end effector 104 having openable/closable jaw members, such a configuration is exemplary and non-limiting and those of ordinary skill in the art would appreciate the instrument 100 can have any of a variety of end effectors without departing from the scope of the present disclosure. In the embodiment of FIG. 1, the force transmission system 110 is coupled to the proximal end portion 111 of the shaft 112. In other embodiments, the force transmission system 110 may be coupled at various locations along the shaft 112, but generally in a position such that it remains external to a remote site (such as a patient's body) at which the end effector 104 and a distal end portion 102 of the shaft 112 are inserted to perform a procedure, thereby permitting access to manipulate inputs on the force transmission system 110. The force transmission system 110 can be configured to be operably coupled with a computer-controlled (e.g., teleoperated) surgical manipulator system, such as the manipulator systems described in further detail below in connection with FIGS. 13 and 14 or similar manipulator systems with which those having ordinary skill in the art are familiar. For example, the force transmission system 110 can be configured to interface with the drive output assembly 1023 of the manipulator system discussed in connection with FIG. 10. In other embodiments, in addition to or in lieu of being configured to interface and be driven by a computer-assisted manipulator system, the force transmission system 110 can be manually controlled with manually operated (e.g., handheld) manipulators, such as triggers, wheels, buttons, joysticks or the like (not shown).

In the embodiment shown in FIG. 1, the instrument 100 includes an articulable structure 105 arranged along the shaft 112 between the end effector 104 and the force transmission system 110. As shown in FIG. 1, the articulable structure 105 can be positioned along the distal end portion 102 of the shaft 112. But the disclosure is not so limited and the articulable structure 105 can be positioned at any location along the shaft 112 without limitation. In addition, the instrument 100 can include more than one articulable structure 105, such as two, three, or more articulable structures located at multiple spaced apart locations along the length of the shaft 112. The articulable structure 105 can be controlled and actuated via actuation members 148, 150 such as cables, rods, or other structures (shown in dashed lines in FIG. 1; further discussed in connection with the various embodiments disclosed herein) operably coupled to a manipulator by a force transmission system. The articulable structure 105 can include one or more joints configured to pivot or flex relative to the shaft 112. In various embodiments, as those having ordinary skill in the art would be familiar with, an articulable structure can serve as a wrist supporting and coupling the end effector 104 to the shaft 112 so as to allow orientation of the end effector 104 relative to the shaft in pitch and/or yaw.

Figure 2:
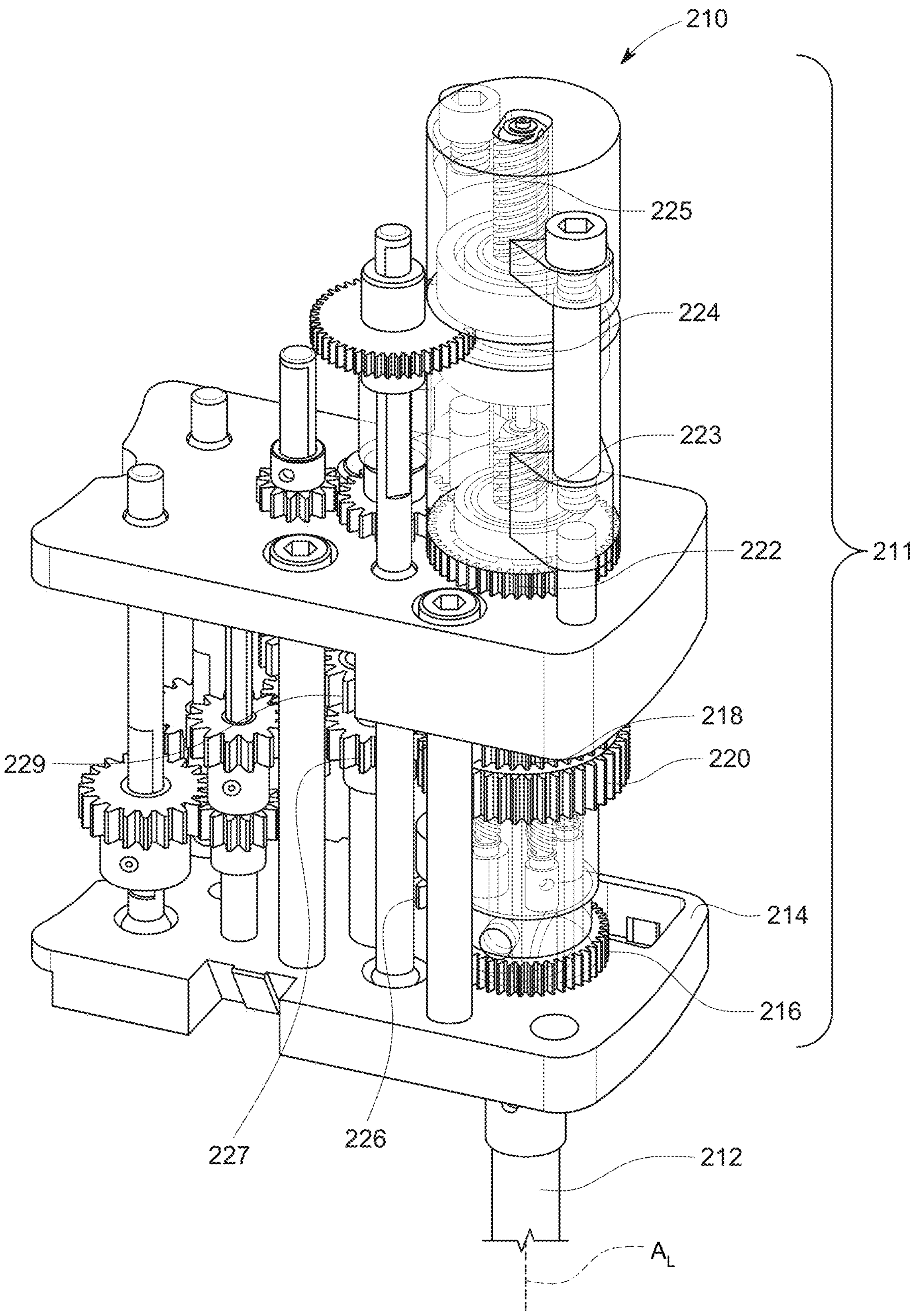
FIG. 2 is a perspective view showing various internal components of a force transmission system according to an embodiment of the present disclosure.

Referring now to FIG. 2, a force transmission system 210 according to various embodiments that can be used as force transmission system 110 is shown. In the embodiment of FIG. 2, the force transmission system 210 is shown without a housing cover of the system removed to better illustrate interior components. As shown in FIG. 2, the force transmission system 210 includes a base chassis 214 to which various components of the force transmission system 210 are coupled. A shaft 212 (e.g., corresponding to shaft 112 in FIG. 1) extends distally from the force transmission system 210 along a longitudinal axis $A_L$.

The force transmission system 210 includes input devices configured to receive input from a manipulator, such as a manipulator that operates with computer assistance (e.g., part of a teleoperated, robotic manipulator system) or a manual manipulator, as noted above. The input devices can be or include, for example, rotary input discs 119 (shown in FIG. 1) or other coupling features configured to engage output drive members of a manipulator of a teleoperated manipulator system to which the force transmission system 210 is couplable, as would be understood by a person having ordinary skill in the art. Each of the input devices is in turn operably coupled with drive components of the force transmission system 210, such as various shafts, gears, and bearings to transmit forces from the input device to the various components of the instrument and shaft 212.

In the embodiment of FIG. 2, the force transmission system 210 includes various drive members coupled with components of the shaft and configured to transmit forces to actuate (e.g., including articulate) actuatable components such as components of the end effector or articulable structures located more distally along the shaft in response to inputs at the input devices of the force transmission system 210, e.g., from a manual or teleoperated manipulator to which the force transmission system 210 is coupled. In addition, the force transmission system 210 can include drive members configured to provide movement to the shaft 212 as a whole, such as roll motion). In the embodiment of FIG. 2, a series of drive members of the force transmission system 210 are arranged coaxially with the shaft 212 and configured to operably engage and be the input drive devices of the force transmission system 210. For example, in the embodiment of FIG. 2, the force transmission system 210 includes an actuation member drive assembly 211 comprising a series of drive members in the form of gears arranged coaxially with the shaft 212 that control roll of the shaft along with force transmission to actuation members (not shown in FIG. 2) to transmit forces along the actuation members to the various movable components (e.g., end effector and/or articulable structures) along the shaft 212.

In the embodiment of FIG. 2, the actuation member drive assembly includes a roll gear 216, a pitch ring gear 218, a yaw ring gear 220, and two actuation gears 222 and 224. The roll gear 216 is rotationally fixed with the shaft 212 such that rotation of the roll gear 216 rotates the shaft 212. The roll gear 216 is engaged with a roll drive gear 226 (partially obscured in FIG. 2) that is operably coupled to an input device (such as an input disc as discussed above) such that rotational forces generated by a manipulator to which the force transmission system 210 is coupled rotate the roll drive gear 226, the roll gear 216, and in turn shaft 212. In the embodiment of FIG. 2, the roll gear 216, the pitch ring gear 218, and the yaw ring gear 220 are arranged in series along the longitudinal axis $A_L$ of the shaft 212 and are coaxial with the shaft 212. In other embodiments, one or more of the roll gear, the pitch ring gear, and the yaw ring gear are arranged non-coaxially with the shaft 212 and/or not coaxial with one another. Further, the order of the roll gear, the pitch ring gear, and yaw ring gear can be changed from the order (relative positioning) shown and described in FIG. 2 embodiment without departing from the general principles discussed herein. While in the embodiment of FIG. 2 the actuation member drive assembly comprises gears as the drive members, it is contemplated with the scope that other mechanisms can be used instead, such as, for example pulleys configured to engage a belt or any other arrangement configured to transmit torque as would be appreciated by one having ordinary skill in the art.

In the embodiment of FIG. 2, the two actuation gears 222 and 224 are configured to transmit force to actuate an end effector (such as end effector 104 shown in FIG. 1) coupled to the shaft 212, such as to actuate grippers, shears, cutting blades, open or close valves (e.g., to deliver suction and/or irrigation), or operate any other actuatable end effector component. The actuation gears 222 and 224 can be operably coupled to drive inputs (such as rotary input discs 119 shown in FIG. 1) of the force transmission system 210 either directly, or, in an arrangement where the drive inputs are located laterally away from the shaft 212, via a series of gears and shafts arranged to transmit rotational input forces from the rotary input discs 119 to the respective actuation gears 222 and 224 similar to the general arrangement described in connection with the roll gear 216. In the embodiment of FIG. 2, the actuation gears 222 and 224 are engaged with associated lead screws 223 and 225 operably coupled with components of the end effector 104 to actuate the instrument 100. For example, the lead screw 223 may be operably coupled to actuate a gripping mechanism (such as one or more jaws) of the end effector 104, and the lead screw 225 may be operably coupled to actuate a cutting mechanism, such as a translating blade (not shown), of the end effector 104. Rotation of the actuation gears 222 and 224 results in translation of the associated lead screws 223 and 225 and actuation of the mechanism to which the lead screw 223 or 225 is operably coupled. For example, each of the actuation gears 222 and 224 can include internal threads (not shown) complementary to and engaged with threads of the respective lead screws 223, 225, such that rotation of each actuation gear 222, 224 causes translation of the respective lead screw 223, 225. While the lead screws 223, 225 are discussed herein as being coupled to gripping and cutting mechanisms, other mechanisms, without limitation, are considered within the scope of the disclosure.

Figure 12:
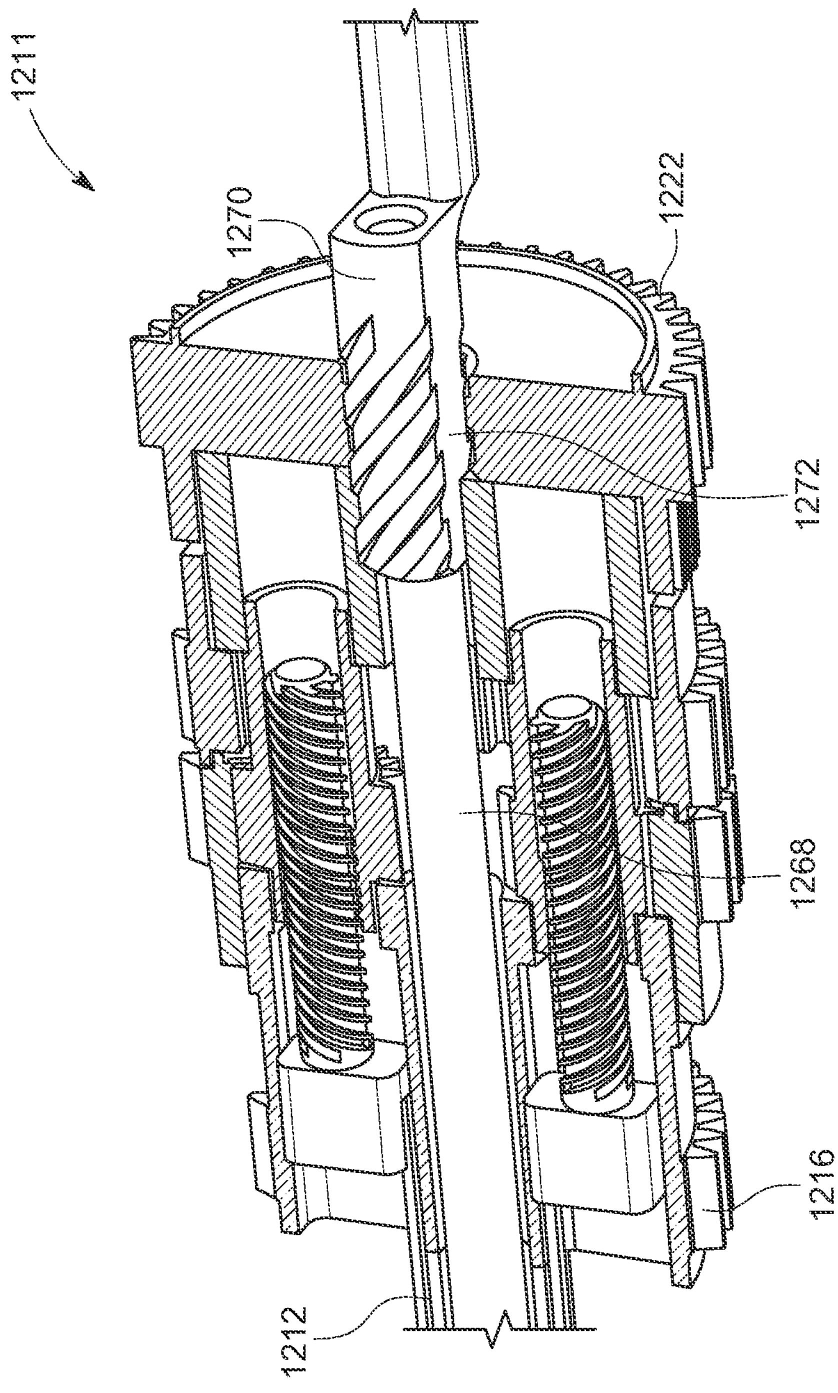
FIG. 12 is a perspective view of an actuation member drive assembly of a force transmission system according to another embodiment of the present disclosure.

In the embodiment of FIG. 2, the actuation gears 222, 224 and the lead screws 223, 225 are rotationally decoupled from roll of the shaft 212 such that roll of the shaft 212 does not cause roll of the lead screws 223, 225 and associated actuation gears 222, 224. In other embodiments of the disclosure, the actuation gears 222, 224 and actuation lead screws 223, 225 can be rotationally coupled with the shaft, such as in the embodiment of FIG. 12 discussed further below.

The pitch ring gear 218 and yaw ring gear 220 are operably coupled to actuation members that extend along the shaft 212 and are operably coupled with an articulable structure of the shaft 212 (such as articulable structure 105 shown in FIG. 1). The actuation of the articulable structure is discussed further in connection with FIGS. 3-7.

Figure 3:
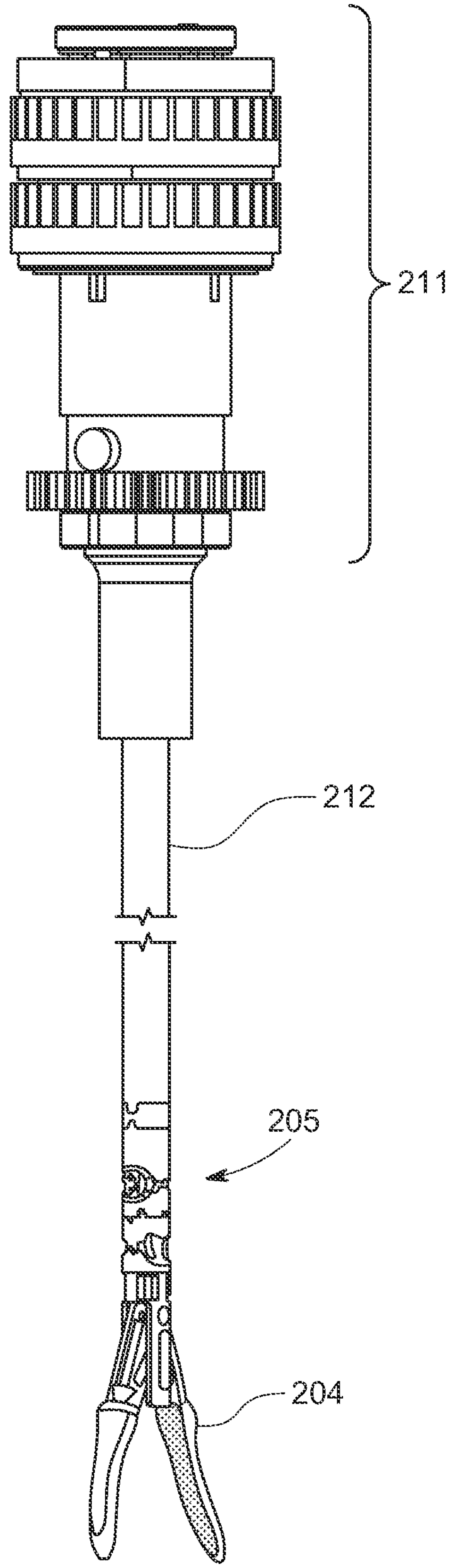
FIG. 3 is a perspective view of an embodiment of an instrument and an actuation member drive assembly of a force transmission system coupled to the instrument shaft according to an embodiment of the present disclosure.

FIG. 3 shows a perspective view of the shaft 212 and actuation member drive assembly 211 of FIG. 2, shown in isolation to better illustrate aspects of thereof. In addition, FIG. 3 shows the entirety of the distal end portion of the instrument, including the end effector 204 and articulable structure 205 (which can be used as end effector 104 and articulable structure 105 of FIG. 1). In some embodiments, the actuation member drive assembly 211 is configured to be removable from the overall force transmission system 210 shown in FIG. 2 to allow for replacement and maintenance and/or to permit interfacing with different manipulator systems, such as the manipulator systems shown and described in connection with FIGS. 13 and 14, and other manipulator systems, including teleoperated manipulators and manual manipulators. For example, as discussed further below, the ring-and-planet gear design and the ability of this design to maintain actuation element tension irrespective of coupling or decoupling from other mechanisms can facilitate such replaceability and modularity.

Figure 4:
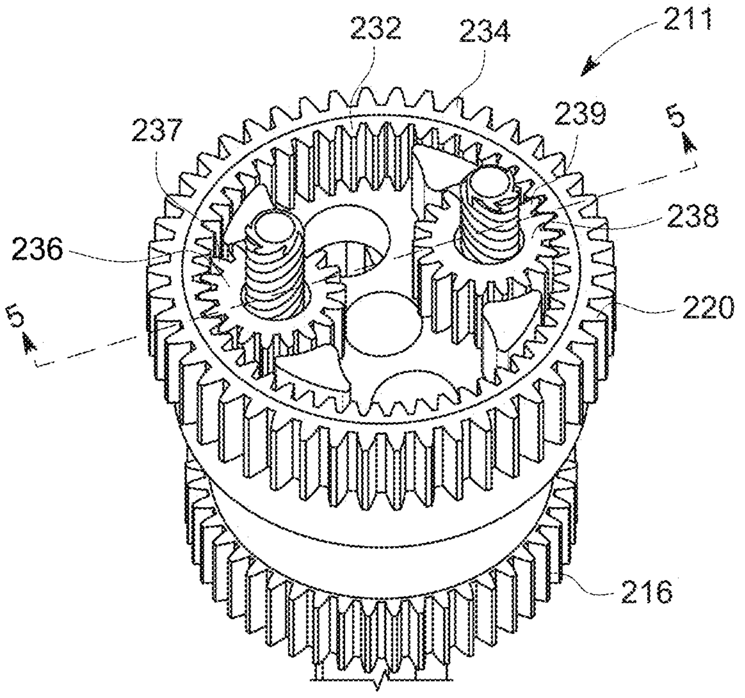
FIG. 4 is a perspective view of various parts of the actuation member drive assembly of FIG. 3.
Figure 5:
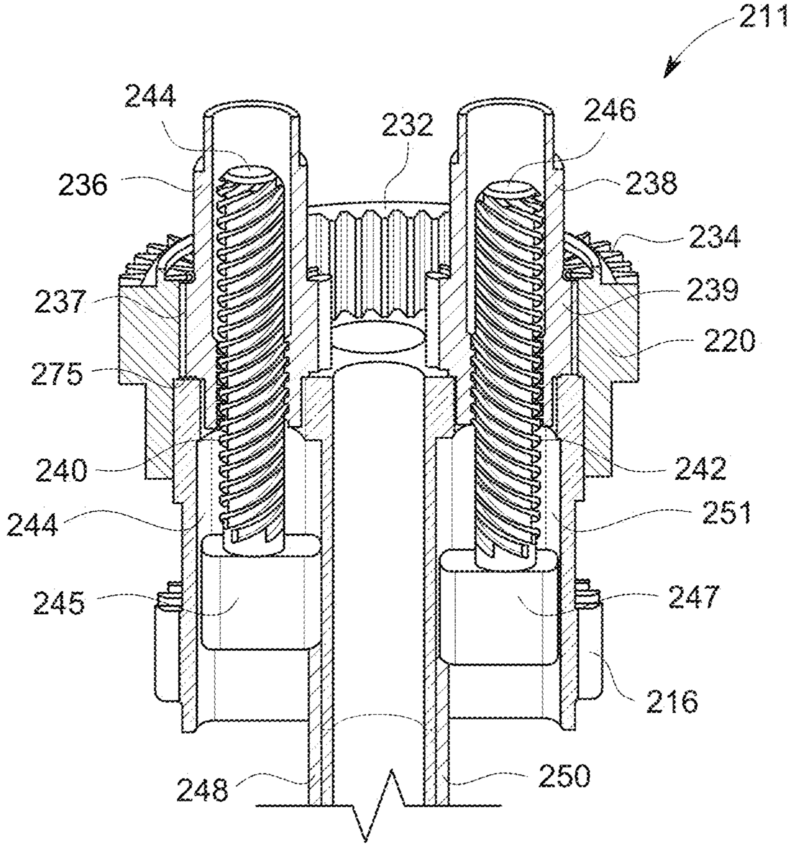
FIG. 5 is a partial sectional view of the actuation member drive assembly of FIG. 4 taken through section 5-5.

Referring now to FIGS. 4 and 5, partial section, detailed perspective views of the actuation member drive assembly 211 are shown to illustrate operational aspects of the assembly. In FIG. 4 and FIG. 5, the pitch ring gear 218 is omitted to better illustrate components associated with the yaw ring gear 220 and its operation, with those of ordinary skill in the art understanding that the operational aspects of the pitch ring gear 218 are similar. The yaw ring gear 220 is a ring gear having inner gear teeth 232 and outer gear teeth 234. The outer gear teeth 234 are configured to be engaged with and driven by an input drive gear 227 FIG. 2; not shown in FIGS. 3-7) operably coupled with an input drive disc (not shown in the view of FIG. 2; e.g., rotary input disc 119 shown in FIG. 1) of the force transmission system 210. Such operable coupling of the rotary input disc 119 with the input drive gear 227 may be via one or more shafts and spur gears, as shown in FIG. 2, or may be via other mechanical arrangements as would be familiar to one of ordinary skill in the art, such as a timing belt, chain drive, or other arrangement.

The yaw ring gear 220 is operably engaged with actuation members such that rotation of the yaw ring gear 220 drives movement of actuation members to transmit force to cause with yaw articulation of an articulable structure of the shaft 212, such as articulable structure 105 (FIG. 1). As discussed above, actuation members can be pull-pull, tension-type actuation members (e.g., cables, filaments, wires, or the like) or push-pull actuation members (e.g., rods or other compression type structures) and are operably coupled to the articulable structure such that application of forces to the members results in articulation of the articulable structure. In the exemplary embodiment of FIGS. 2-7, the instrument includes a first pair of actuation members 248, 250 arranged such that translating each of the pair of actuation members in opposite directions places the actuation member 248, 250 in tension to transmit forces to cause articulation in the yaw degree of freedom of the articulable structure 205 (FIG. 3).

More specifically, the actuation member drive assembly 211 is configured such that rotation of the yaw ring gear 220 causes each actuation member 248, 250 of the first pair of actuation members to translate in opposite directions to achieve a pay-in/pay-out coordinated movement to result in the articulation of the articulable structure 205, as those of ordinary skill in the art would be familiar with. To accomplish this coordinated movement, the embodiment of FIGS. 2-7 includes first and second yaw planet gears 236 and 238 arranged within and operably engaged with the yaw ring gear 220. The first and second yaw planet gears 236 and 238 each have external teeth 237, 239 meshed with the inner gear teeth 232 of the yaw ring gear 220 such that rotation of the yaw ring gear 220 results in corresponding rotation of the first and second yaw planet gears 236 and 238. In the embodiment of FIGS. 4-7, the first and second yaw planet gears 236 and 238 are positioned diametrically opposite one another. However, this arrangement is optional and the first and second yaw planet gears 236, 238 can be positioned at different locations (i.e., not diametrically opposite) around the yaw ring gear 220.

Each of the first yaw planet gear 236 and second yaw planet gear also includes internal threading 240, 242. The internal threading 240 of the yaw planet gear 236 is engaged with a first yaw lead screw 244, and the internal threading 242 of the yaw planet gear 238 is engaged with a second yaw lead screw 246. The first yaw lead screw 244 is operably coupled to the first actuation member 248 and the second yaw lead screw 246 is operably coupled to the second actuation member 250. The first yaw lead screw 244 and second yaw lead screw 246 each also comprise one or more key portions 245 and 247 that ride in correspondingly shaped cavities 249 and 251. The key portions 245 and 247 are configured such that they cannot rotate within the cavities 249 and 251, thereby ensuring that rotation of the yaw planet gears 236, 238 occurs relative to the yaw lead screws 244, 246 and causes translation of the yaw lead screws 244, 246 and actuation members 248, 250.

To achieve coordinated pay in/pay out motion of the two actuation members 248, 250 (i.e., simultaneous translation of the first actuation member 248 and second actuation member 250 in opposite directions to articulate the articulable structure 205 (FIG. 2), the threaded engagement of the internal threading 240 of the first yaw planet gear 236 and the first yaw lead screw 244 and the threaded engagement of the internal threading 242 of the second yaw planet gear 238 and second yaw lead screw 246 are in opposite orientations (e.g., clockwise pattern versus counterclockwise pattern). Due to the opposite orientations of the threaded engagements, rotation of the yaw ring gear 220 results in the yaw lead screws 244, 246 moving in opposite directions in response to the rotation of the yaw planet gears 236, 238, in turn causing translation of the first actuation member 248 and second actuation member 250 in opposite directions to effect articulation of the articulable structure 105 in yaw degree of freedom relative to the shaft 212.

In various embodiments of the disclosure, the first actuation member 248 and the second actuation member 250 can comprise one or more sheets of material, in comparison to conventional designs in which the actuation members comprise tension-type actuation members such as cables and the like that are flexible. Because the first actuation member 248 and second actuation member 250 are coupled directly to lead screws 244, 246, the first and second actuation members 248, 250 are not required to undergo complex routing and changes of direction within the force transmission system, the first and second actuation members 248, 250 are not required to have as high a degree of flexibility compared to conventional stranded cables, thereby facilitating use of sheet material or other actuation members other than stranded cables or other highly flexible structures. Using sheet material, such as sheet metal, for the actuation members 248, 250 can result in cost saving and can simplify manufacture of the force transmission system 210. However, the current disclosure is not so limited, and cable-type actuation members can be used with the present disclosure, including stranded cables and other tendon-type structures. Such embodiments still provide advantages in manufacturability over conventional designs due to the reduction in complexity of routing the members and the actuation member tensioning method discussed below. Finally, because the actuation members are rotated as a part of the overall actuation member drive assembly, the actuation members are not subjected to a wrapping effect that may contribute to excess friction and wear of actuation members in instrument configurations in which the actuation members wrap around the shaft as the shaft is rotated.

Figure 6:
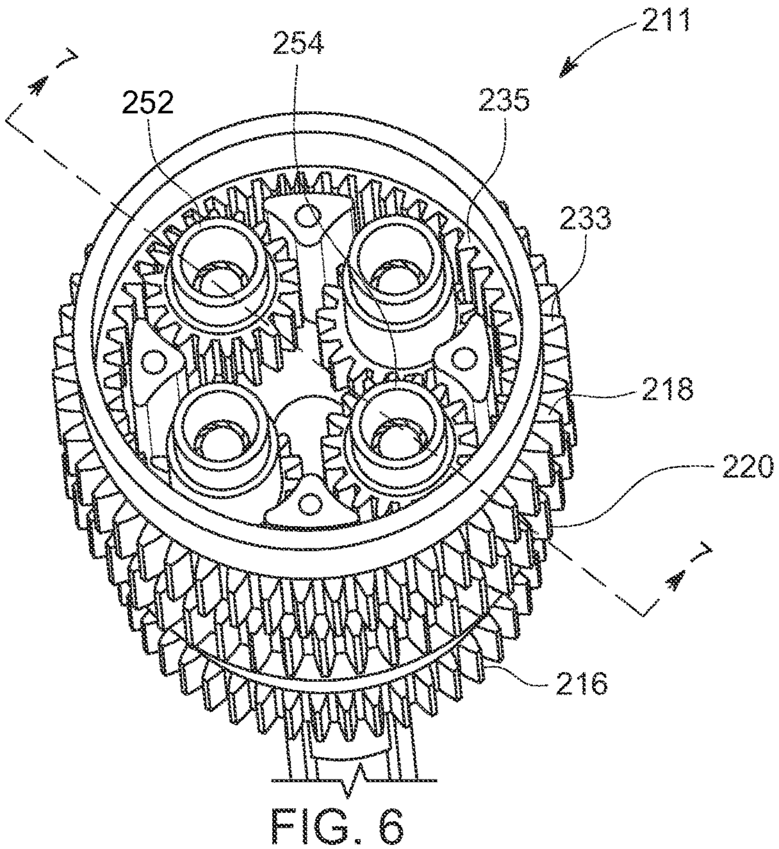
FIG. 6 is another perspective view of various parts of the actuation member drive assembly of FIG. 3.
Figure 7:
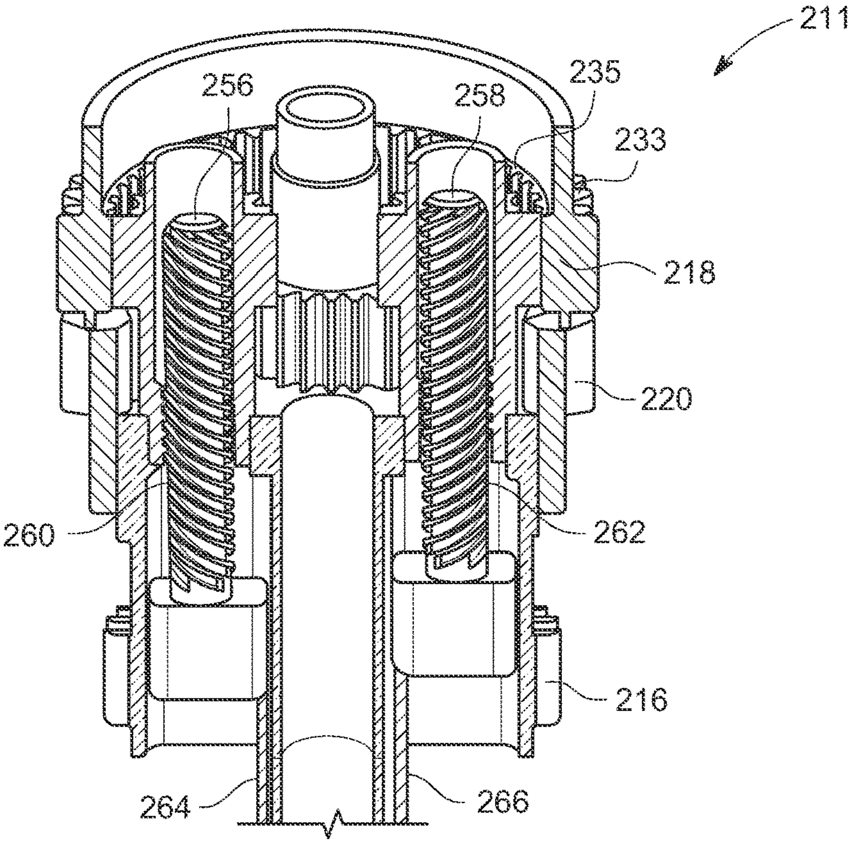
FIG. 7 is partial sectional view of the actuation member drive assembly of FIG. 6 taken through section 7-7.

FIGS. 6 and 7 show partial section, detailed perspective views of the actuation member drive assembly 211 with the pitch ring gear 218 and associated componentry shown. The pitch ring gear 218 is arranged coaxially with the longitudinal axis of the shaft 212 in a stacked arrangement with the yaw ring gear 220. The pitch ring gear 218 can be configured similarly to the yaw ring gear 220, comprising outer gear teeth 233 and inner gear teeth 235. The outer gear teeth 233 are configured to be engaged with a pitch drive gear 229 (FIG. 2) operably coupled with an input disc of the force transmission system 210 in a manner similar to that discussed above in connection with the yaw ring gear 220.

A first pitch planet gear 252 and a second pitch planet gear 254 are meshed with the inner gear teeth 235 of the pitch ring gear 218. A first pitch lead screw 256 is engaged with first internal threads 260 of the first pitch planet gear 254, and a second pitch lead screw 258 is engaged with second internal threads 262 of the second pitch planet gear. The first pitch lead screw 256 is coupled to a third actuation member 264 and the second pitch lead screw 258 is coupled to a fourth actuation member 266. The third actuation member 264 and the fourth actuation member 266 are operably coupled to an articulable structure, such as articulable structure 105 (FIG. 1) such that actuation of the third actuation member 264 and the fourth actuation member 266 results in articulation of the articulable structure 105 in a pitch degree of freedom, as discussed in more detail hereinafter. The third actuation member 264 and fourth actuation member 266 can comprise sheet material, similar to the first and second actuation members 248, 250.

Similar to the arrangement of the yaw ring gear 220 and the associated yaw planet gears and yaw lead screws, the threads of the first pitch planet gear 252 and first pitch lead screw 256 can extend in a first helical direction, and the threads of the second pitch planet gear 254 and the second pitch lead screw 258 extend in a second helical direction opposite the first direction. Accordingly, rotation of the pitch ring gear 218 ultimately results in translation of the first pitch lead screw 256 in a first direction and translation of the second pitch lead screw 258 in a second direction opposite the first direction. Translation of the first pitch lead screw 256 in the first direction causes translation of the third actuation member 264 in the first direction, and translation of the second pitch lead screw 258 in the second direction causes translation of the fourth actuation member 266 in the second direction. Translation of the third and fourth actuation members 264, 266 in opposite directions causes articulation of the articulable structure 205 (FIG. 2) in a pitch degree of freedom.

While the embodiment of FIGS. 2-7 is shown with a pitch ring gear 218 and yaw ring gear 220 and the associated components supporting two degrees of freedom of movement of the shaft 212, in other embodiments fewer or more degrees of freedom can optionally be provided using the same basic architecture. In one non-limiting example, an instrument can optionally include multiple articulable structures, each with multiple degrees of freedom. For example, one embodiment could include two articulable structures, each having pitch and yaw degrees of freedom, in which case a actuation member drive assembly would include two yaw ring gears and two pitch ring gears, each being associated with a separate degree of freedom of each articulable structure. Other combinations, such as one or more articulable structures with a single degree of freedom or multiple degrees of freedom and any other combination, are within the scope of the disclosure. Those of ordinary skill in the art would understand from the present disclosure and illustrated embodiments how to achieve various other permutations using the basic architecture of ring gears, planet gears, and lead screws described above, e.g., by using additional sets of ring gears, planet gears, lead screws, actuation members, etc. Further, each of the degrees of freedom of movement can be independently actuated simultaneously or non-simultaneously with other degrees of freedom of movement to obtain the desired position and orientation of the end effector.

As noted above, the roll gear 216 is fixedly coupled to the shaft 212 such that rotation of the roll gear 216, e.g., driving the roll gear 216 with the roll drive gear 226 discussed in connection with FIG. 2 results in rotation of the entire shaft 212 about its longitudinal axis (referred to as rolling the shaft). Because the actuation members run through the shaft 212, it is desirable to ensure that rolling the shaft does not result in relative rotation of the ring gear, which could in turn result in unintended actuation of the actuation members. To address this potential issue, it is desirable to ensure that the gears to which the actuation members are connected (e.g., pitch and/or yaw gears) rotate together around the longitudinal axis of the shaft with the roll gear. In some embodiments, this can be accomplished by including software and/or hardware features that maintain an articulated position of the articulable structure 205 during roll of the shaft 212. For example, in embodiments in which the instrument 100 (FIG. 1) is coupled to a computer assisted (e.g., teleoperated) manipulator system, such as the manipulator systems described in connection with FIGS. 13 and 14, the manipulator can be programmed so that when the roll gear 216, is driven, the pitch and yaw gears 218, 220 are driven at the same rate as the roll gear 216 such that the roll gear 216, pitch gear 218, and yaw gear 220 rotate together as an assembly, thereby preventing any undesired movement of the associated lead screws. In other words, the manipulator can be programmed to rotate the pitch and yaw gears 218, 220 as the roll gear 216 rotates such that the pitch and yaw gears 218, 220 remain in the same orientation with the roll gear 216 and the shaft 212 as the roll gear 216 is rotated.

In some embodiments, as an alternative to programming the manipulator to rotate the pitch and yaw gears 218, 220 with rotation of the roll gear 216 to maintain the articulated position of the articulable structure 205, the manipulator system can include mechanical features configured to maintain the positioning of the articulable structure 205 (FIG. 3) during rotation of the shaft. For example, the force transmission system 210 can include one or more mechanical differentials that couple the pitch and yaw ring gears 218 and 220 with the roll gear 216 such that driving the roll gear 216 also results in driving the pitch and yaw gears 218 and 220 at the same angular speed, while permitting driving of the pitch ring gear 218 and/or yaw ring gear 220 without a corresponding rotation of the roll gear 216. For example, an arrangement including mechanical differentials is disclosed in U.S. Pat. No. 10,710,246 (filed Aug. 12, 2015), the entire contents of which is incorporated by reference herein.

Due to the interlocking nature of the ring gears and associated planet gears and lead screws, for example yaw ring gear 220 being meshed with the yaw planet gears 236 and 238, which are engaged with the yaw lead screws 244 and 246, any tension applied to the associated actuation members 248, 250 can be isolated to the actuation member drive assembly 211. Stated another way, a tensile force applied to the first and second actuation members 248, 250, e.g., a preload force applied during manufacturing, is maintained by the engagement of the yaw ring gear 220 with the yaw planet gears 236 and 238, without being applied to the various drive components of the force transmission system 210 (FIG. 3) other than the yaw ring gear 220. Likewise, tension applied to the third and fourth actuation members 264, 266 is maintained through engagement of the pitch planet gears 252, 254 with the pitch ring gear 218, and a pre-tension force applied to the third and fourth actuation members 264, 266 is not experienced by drive components of the force transmission system 210 other than the pitch ring gear 218.

This ability to lock the actuation members in position by the geared/lead screw arrangement facilitates removal of the actuation member drive assembly 211 from the other components of the overall force transmission system 210 without releasing the pretension force. In this way, the shaft and actuation member drive assembly can be easily removed and replaced for servicing or swapped from a force transmission system configured to couple to a first type of manipulator to a force transmission system configured to couple to a second type of manipulator, including swapping between manual (e.g., handheld) and computer-assisted (e.g., teleoperated) manipulators, as discussed above.

As further discussed below, the actuation member drive assembly 211 is configured such that a preload tension force applied to the actuation members is maintained within the actuation member drive assembly 211 and not applied to other components of the force transmission system 210. By isolating the preload tension force to the actuation member drive assembly 211, the actuation member drive assembly 211 can be removed from and replaced in various force transmission systems as discussed above without releasing the preload tension force.

Moreover, by isolating the pretension force to the actuation member drive assembly 211, manufacturing steps for assembling the force transmission system and overall instrument can be more amenable to automated assembly and production. For example, in conventional designs in which actuation members are in the form of cables following a complex path through the force transmission system from the shaft to a capstan or pulley coupled to an input device, routing and tensioning the actuation members can be a complicated process that is less suitable to automating the manufacturing. FIGS. 8-11C illustrate various aspects and components of a force transmission system according to the present disclosure that facilitates automation of the manufacturing process, including assembly and tensioning of the actuation members.

Figure 8:
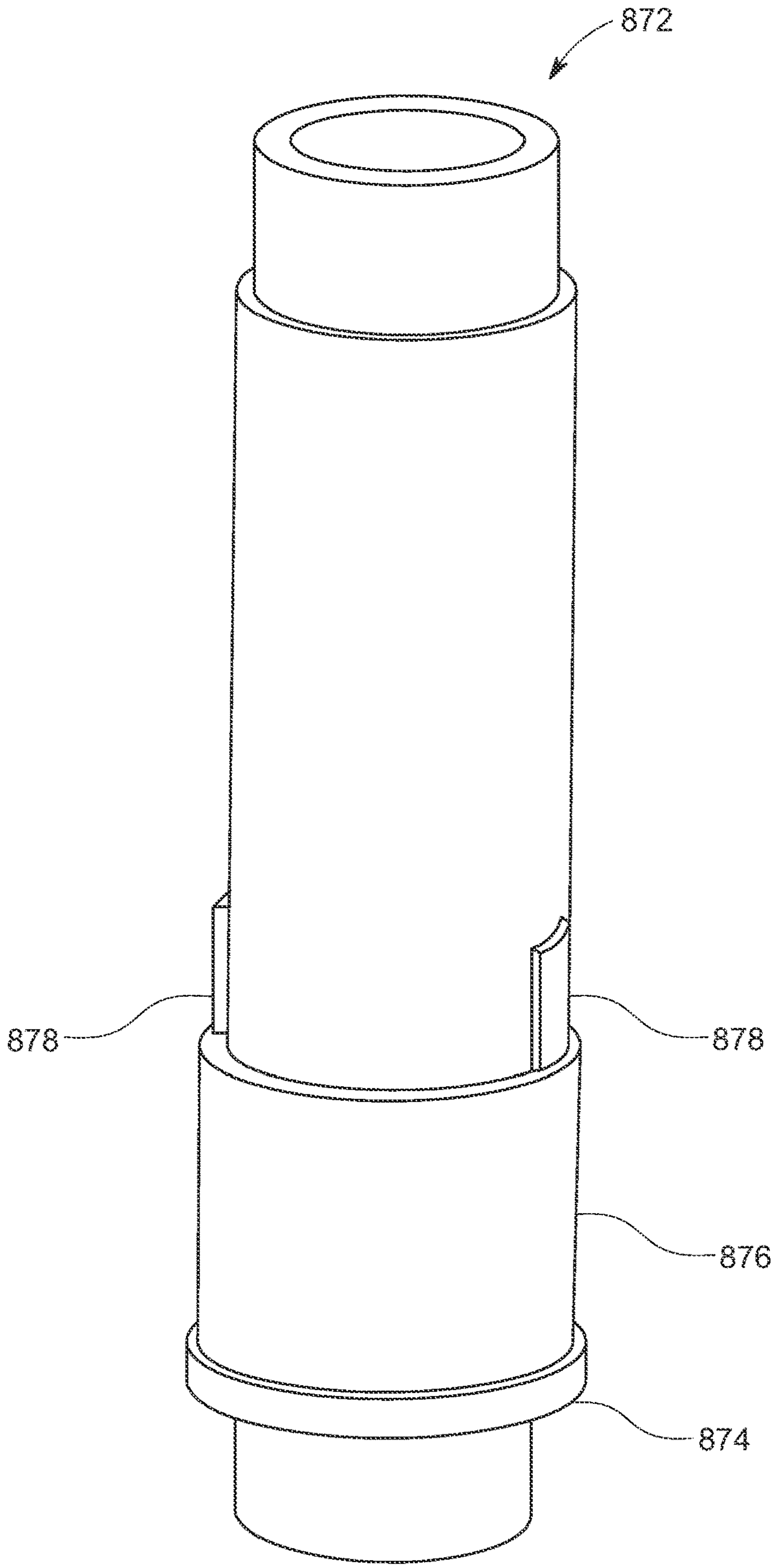
FIG. 8 is a perspective view of a component of the actuation member drive assembly of FIG. 3.

In some embodiments, elements of the actuation member drive assembly comprise multiple components that facilitate automated assembly and tensioning of the actuation members. For example, in some embodiments, the planet gears, such as the first and second pitch planet gears and/or the first and second yaw planet gears, each comprise an inner member and an outer member. Referring now to FIG. 8, a planet gear inner member 872 is shown in perspective view. The planet gear inner member 872 can be used with any of the planet gears discussed herein, such as the first and second yaw planet gears and first and second pitch planet gears. The planet gear inner member 872 comprises a generally tubular shape that includes a distal thrust surface portion 874, a shank portion 876, and one or more key features 878 extending proximally from the shank portion 876. The shank portion 876 has an outer diameter larger than an outer diameter of a portion of the planet gear inner member 872 that includes the one or more key features 878. The planet gear inner member 872 includes internal threads (not visible in FIG. 8) configured to engage an associated lead screw, as shown in the cross-sectional views of FIGS. 5 and 7.

Figure 9:
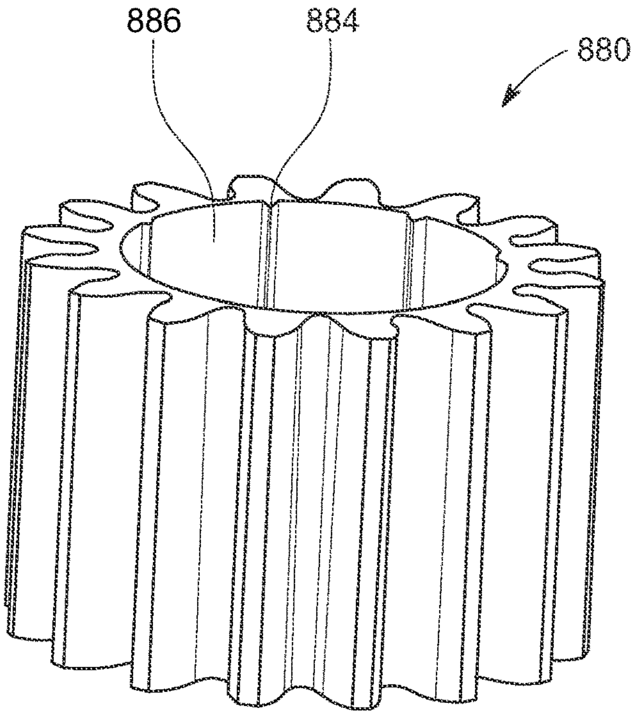
FIG. 9 is a perspective view of another component of the actuation member drive assembly of FIG. 3.
Figure 10:
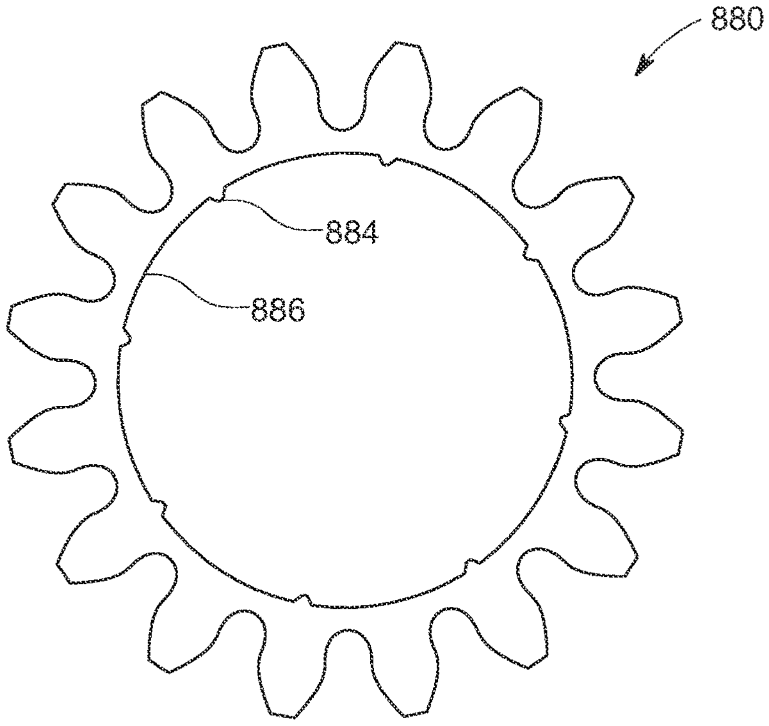
FIG. 10 is a top view of the component of FIG. 9.

The shank portion 876 is configured to receive a planet gear outer member 880, shown in FIGS. 9 and 10. The planet gear outer member 880 includes external gear teeth 882 configured to mesh with a ring gear, such as a yaw ring gear or a pitch ring gear. The planet gear outer member 880 also includes longitudinal splines 884 arranged in a bore 886 of the planet gear outer member 880. The bore 886 is configured to receive the shank portion 876 of the planet gear inner member 872. The longitudinal splines 884 are configured to generate and/or promote an interference fit between the shank portion 876 of the planet gear inner member 872 and the planet gear outer member 880 such that the planet gear inner member 872 and the planet gear can be coupled to one another during a manufacturing procedure, as discussed in connection with FIGS. 11A-C.

Figure 11A:
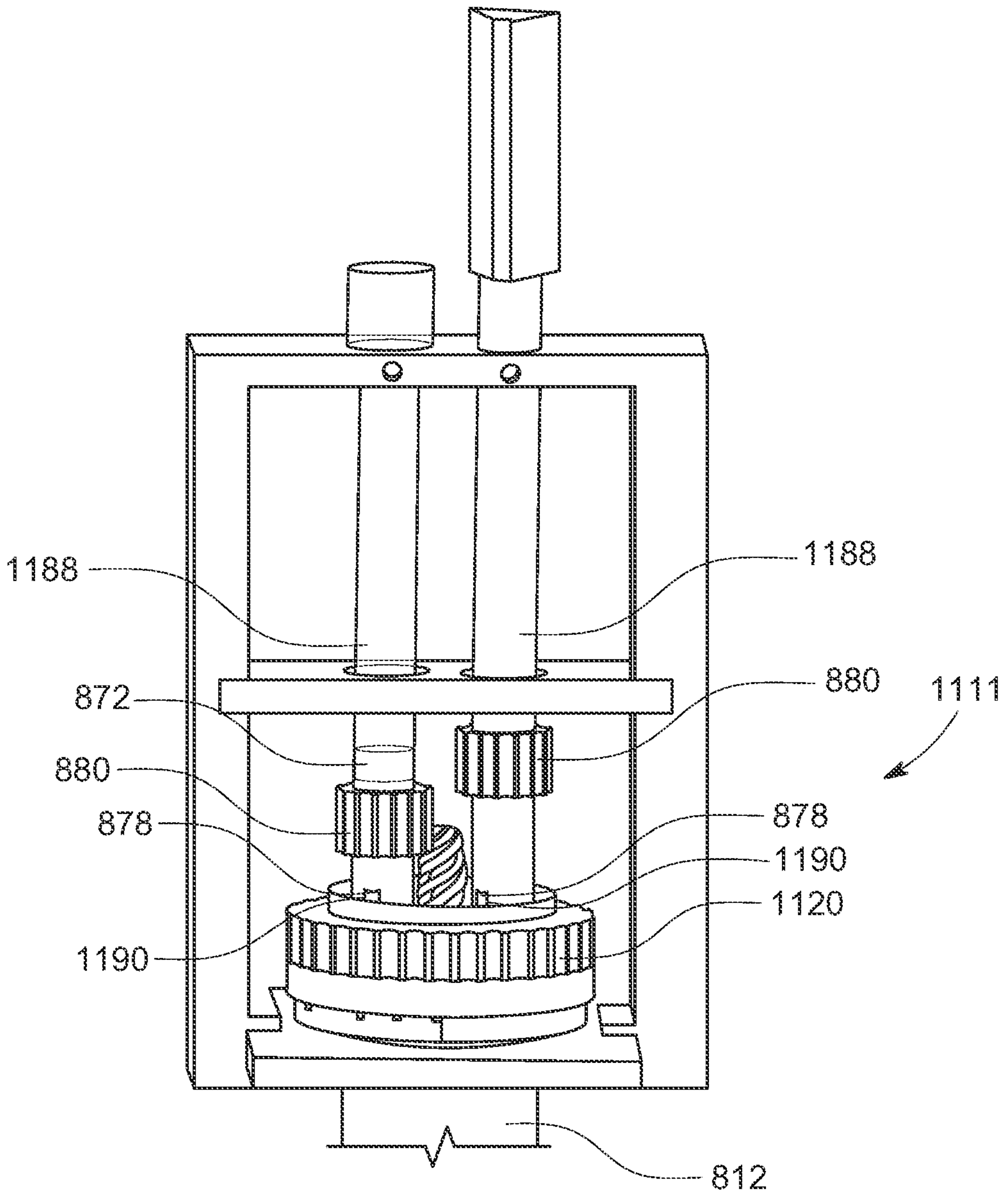
FIG. 11A is a perspective view depicting an assembly device assembling the drive assembly of FIG. 3.
Figure 11B:
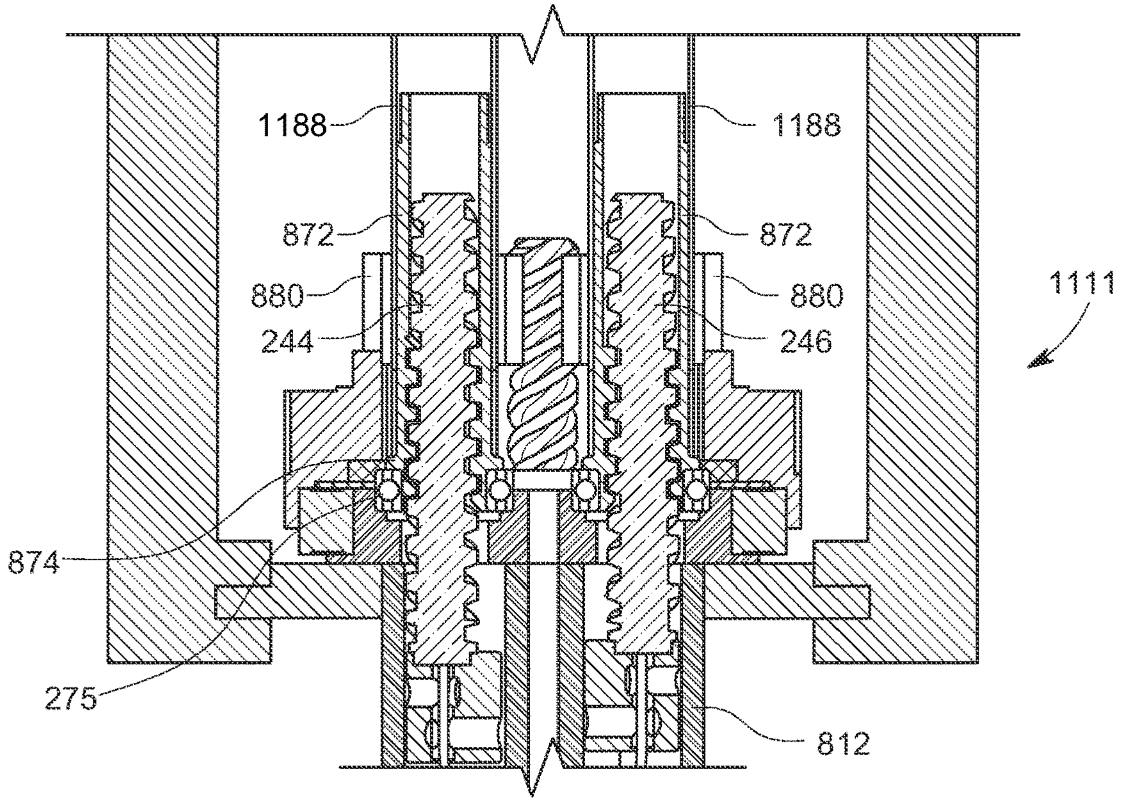
FIGS. 11B and 11C are cross-sectional views of the assembly device and drive assembly of FIG. 3.
Figure 11C:
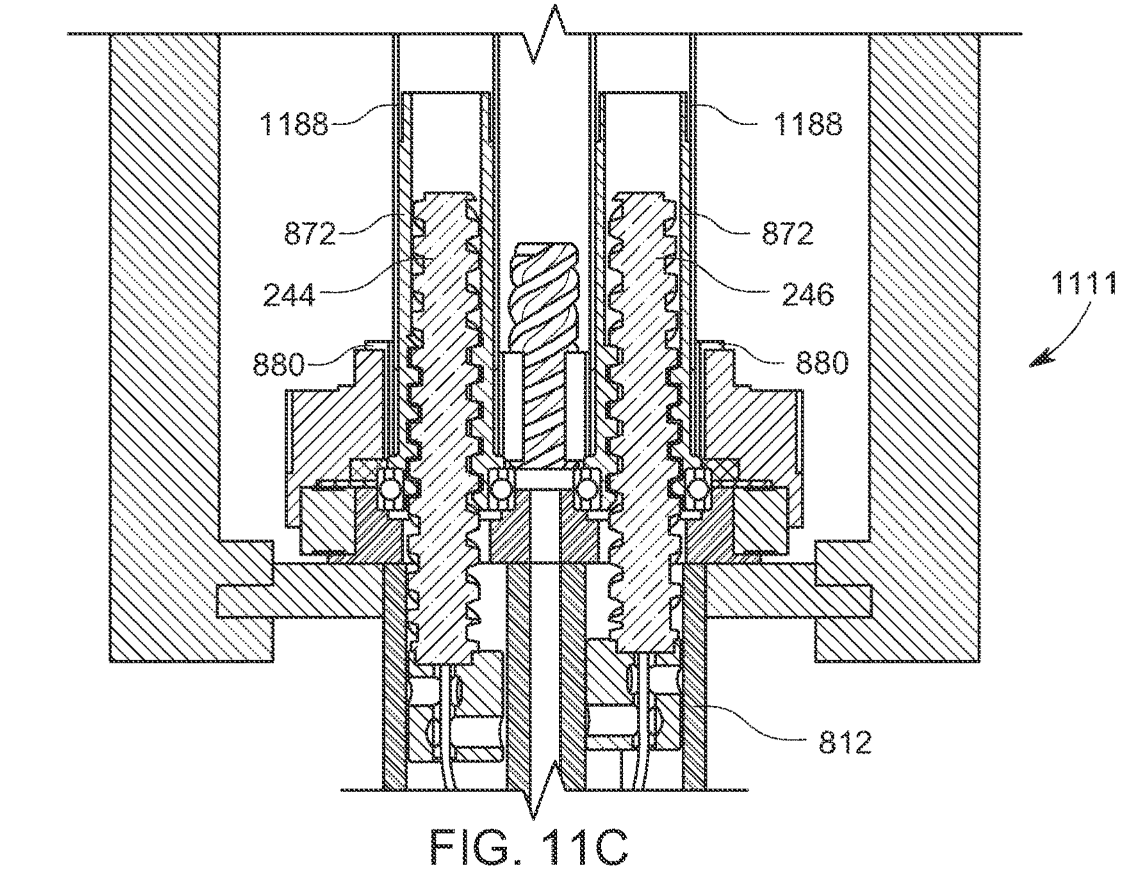

Referring now to FIGS. 11A-C, an actuation member drive assembly 1111 is shown in a state of partial assembly to illustrate a method of tensioning and assembling the actuation member drive assembly 1111. The planet gear inner members 872 are threaded over their associated lead screws 244, 246, such as by hand or by powered and/or automated mechanisms, such as rotational drivers 1188. Each of the lead screws is assembled with an associated actuation member coupled to the articulable structure of the instrument (e.g., 205 in FIG. 2). The rotational drivers 1188 include notches 1190 configured to engage with the key features 878 of the planet gear inner members 872. The rotational drivers 1188 can be configured to apply a desired level of torque to the planet gear inner members 872. As the planet gear inner members 872 are tightened, the distal thrust surface 874 (FIG. 8) bears against a corresponding internal shoulder 275 (also shown in FIG. 5; in FIGS. 11B and 11C, the internal shoulder 275 is a bearing inner race) of the shaft 812 generating a tensile force in the actuation member associated with the lead screw.

Once the tension in the actuation member reaches the desired level, which can be determined, e.g., by measuring the torque applied to the planet gear inner member 872, measuring the tension of the actuation member via a strain gauge, or measuring deflection of the actuation member under a known lateral test load applied to the actuation member, or another method as would be apparent to a person of ordinary skill in the art, the planet gear outer member 880 is advanced over the planet gear inner member 872 until the shank portion 876 (FIG. 8) of the planet gear inner member 872 is received within the bore 886 (FIGS. 9 and 10) of the planet gear outer member 880. In the embodiment of FIGS. 11A-11C, the shank portion 876 of the planet gear inner member 872 has a greater diameter than the portion of the planet gear inner member 872 engaged by the rotational drivers 1188, and greater than a diameter of the rotational drivers 1188 themselves. This configuration enables the planet gear outer member 880 to be advanced over the rotational driver 1188 and onto the shank portion 876 of the planet gear inner member 872 while the rotational driver 1188 is in place on the planet gear inner member 872.

As the planet gear outer member 880 advances further over the shank portion 876, slight rotational adjustment of the now partially assembled planet gear inner member 872 and planet gear outer member 880 may further align the external gear teeth 882 of the planet gear outer member 880 to mesh with the internal teeth of the yaw ring gear 1120 if needed. In the embodiment of FIGS. 11A-11C, the yaw ring gear 1120 is a yaw ring gear corresponding to the yaw ring gear 220 shown in FIGS. 2-7. However, the process described in connection with FIGS. 11A-11C can also be used to assemble and tension components relating to the pitch degree of freedom, e.g., pitch ring gear 218 and the associated components shown in FIGS. 2-7.

Once the external gear teeth 882 of the planet gear outer member 880 are aligned with the internal teeth of the yaw ring gear 1120, the planet gear outer member 880 can be fully pressed into place over the shank portion 876 of the planet gear inner member 872, i.e., to the fully assembled condition shown in FIG. 11C. Once both planet gears are in assembled condition, e.g., as shown in FIG. 11C, the engagement of the assembled first yaw planet gear 236 and assembled second yaw planet gear 238 with the yaw ring gear 1120 ensure the tension applied to the actuation members associated with each lead screw is maintained. For example, as discussed above, since the lead screws and associated planet gears are threaded in opposite directions, the tension applied to each will be maintained by engagement of each planetary gear with the ring gear.

In some exemplary embodiments, the planet gear inner member 872 comprises a material having a higher ductility than a material of the planet gear outer member 880, so that the longitudinal splines 884 (FIGS. 9 and 10) deform the planet gear inner member 872 as the planet gear outer member 880 is pressed over the shank portion 876 (FIG. 8) of the planet gear inner member to rotationally lock the planet gear inner member 872 and planet gear outer member 880 together.

For example, in one embodiment, the planet gear inner member 872 can comprise a polymer material, and the planet gear outer member 880 can comprise a metal alloy exhibiting greater hardness than the polymer material of the planet gear inner member 872. In other embodiments, the planet gear inner member 872 can also comprise a metal alloy more ductile than the metal alloy of the planet gear outer member 880. In yet other embodiments, the longitudinal splines may be formed on the planet gear inner member 872, and the materials can be chosen such that the hardness of the planet gear outer member 880 is less than the hardness of the planet gear inner member 872.

In other embodiments, the longitudinal splines may be omitted and the planet gear inner member 872 and planet gear outer member 880 may be coupled only via interference fit, or may be coupled by an interference fit or a slip fit in conjunction with other acts or processes to rotationally couple the planet gear inner member 872 and planet gear outer member 880, such as application of adhesives, welding processes (laser welding, arc welding) or other approaches as would be apparent to a person skilled in the art to couple the planet gear inner member 872 and planet gear outer member 880.

As discussed in connection with the embodiment of FIG. 2, the actuation gears 222, 224 and the lead screws 223, 225 are rotationally isolated from the shaft 212 such that roll of the shaft 212 does not cause rotation of the lead screws 223, 225 and associated actuation gears 222, 224. In other embodiments of the disclosure, components associated with actuation of the end effector or other components of the instrument can be coupled to roll with the shaft 212. Such an arrangement may be useful for the actuation of actuation members that are centrally routed through the instrument shaft. For example, referring now to FIG. 12, another embodiment of an actuation member drive assembly 1211 is shown. In this embodiment, the actuation member drive assembly 1211 includes a grip drive gear 1222 operably coupled to a centrally routed push/pull type actuation member (which may be in the form of a rod or other relatively stiff member configured to drive translation of actuating components that may be associated with relatively higher forces to operate them, such as to actuate jaw members to open and close (grip actuation) or translating elements that may go through tissue such as translating cutting elements and/or staple drivers. While the grip drive gear 1222 is described in connection with a grip function herein, the grip drive gear 1222 can alternatively be a drive gear associated with any other type of function of an end effector. The grip drive gear 1222 is engaged with a lead screw portion 1270 that is in turn connected to a push/pull grip actuation member 1268. The grip actuation member 1268 extends through the shaft 1212 distally to an end effector portion (such as end effector 104 shown in FIG. 1) and is engaged with a component of the end effector. To prevent the grip actuation member 1268 from rotating relative to the shaft 1212 when actuation torque is applied to the grip drive gear 1222, the grip actuation member 1268 can include anti-rotation features. For example, the grip actuation member 1268 can include one or more flattened key surfaces 1272 that interface with portions of the shaft 1212 to prevent rotation of the grip actuation member 1268 when torque is applied to the grip drive gear 1222. To prevent overall rotation (i.e., roll) of the shaft 1212 from affecting the actuation of the grip actuation member 1268, the instrument and manipulator system can include software and/or hardware features that effectively rotationally couple the grip drive gear 1222 with the shaft 1212 in a manner similar to that discussed above in relation to maintaining the relative pitch and yaw positioning during rotation of the shaft. For example, in computer-assisted (e.g., teleoperated) manipulator embodiments, the manipulator can drive rotation of the shaft 1212 via roll gear 1216 and, simultaneously, rotate the grip drive gear 1222 at the same angular rate to maintain the relative orientation between the shaft 1212 and the grip drive gear 1222, thereby preventing any change in position of the grip actuation member 1268 relative to the shaft 1212.

Various embodiments of the present disclosure provide force transmission systems that facilitate modular and automated assembly and adaptability to various applications. Further, they can facilitate overall manufacturing, assembly, and contribute to reliability of the device.

Embodiments described herein may be used, for example, with remotely operated, computer-assisted systems (such, for example, teleoperated surgical systems) such as those described in, for example, U.S. Pat. No. 9,358,074 (filed May 31, 2013) to Schena et al., entitled "Multi-Port Surgical Robotic System Architecture", U.S. Pat. No. 9,295,524 (filed May 31, 2013) to Schena et al., entitled "Redundant Axis and Degree of Freedom for Hardware-Constrained Remote Center Robotic Manipulator", and U.S. Pat. No. 8,852,208 (filed Aug. 12, 2010) to Gomez et al., entitled "Surgical System Instrument Mounting", each of which is hereby incorporated by reference in its entirety. Further, embodiments described herein may be used, for example, with various da Vinci® Surgical Systems, commercialized by Intuitive Surgical, Inc., of Sunnyvale, California.

The embodiments described herein are not limited to the surgical systems noted above, and various other teleoperated, computer-assisted surgical system configurations may be used with the embodiments described herein. Further, although various embodiments described herein are discussed in connection with a manipulating system of a teleoperated surgical system, the present disclosure is not limited to use with a teleoperated surgical system. Various embodiments described herein can optionally be used in conjunction with hand-held, manual instruments.

Figure 13:
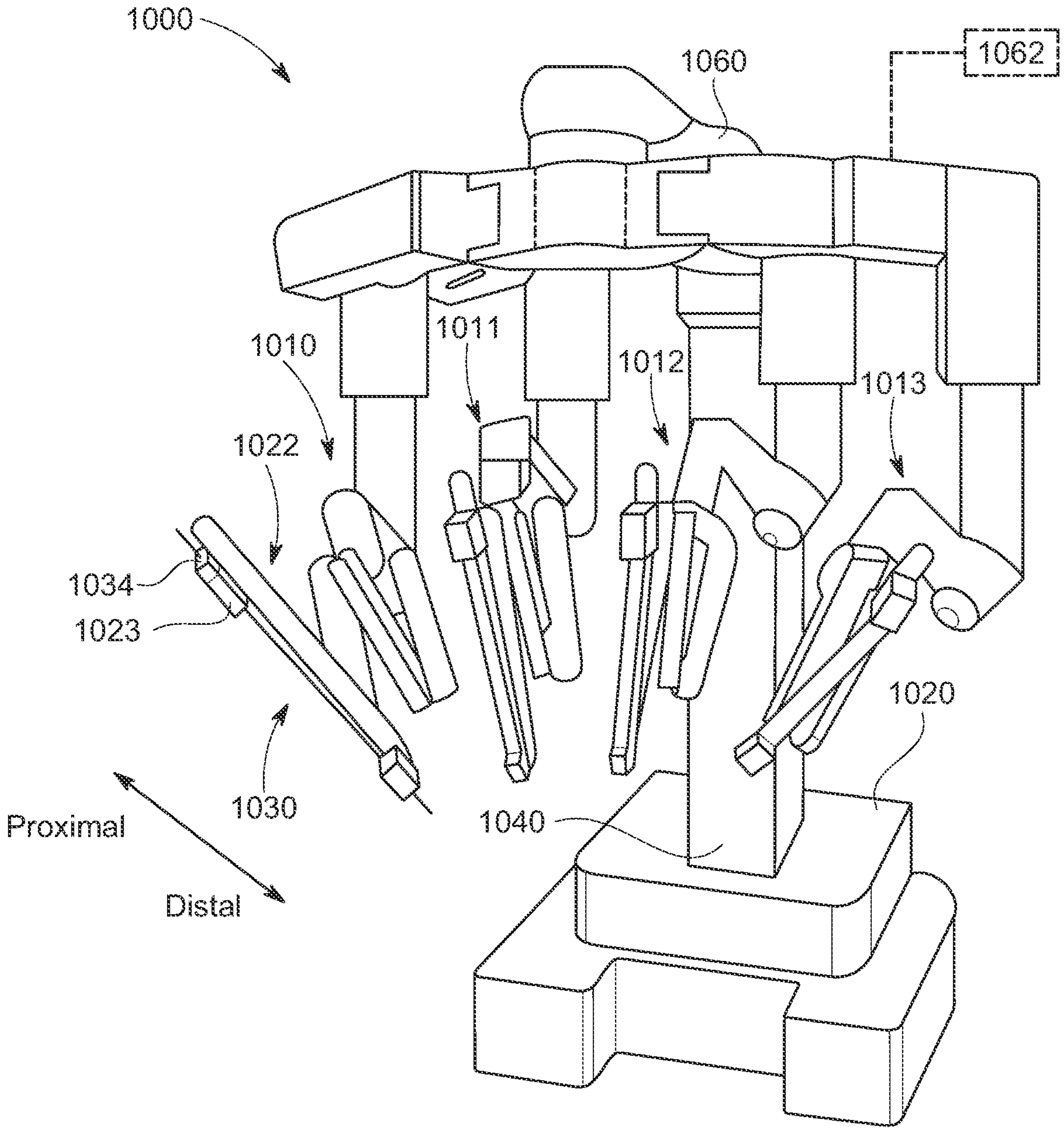
FIG. 13 is a perspective schematic view of a manipulator system according to some embodiments of the present disclosure.

As discussed above, in accordance with various embodiments, force transmission systems of the present disclosure are configured for use in teleoperated, computer-assisted surgical systems employing robotic technology (sometimes referred to as robotic surgical systems). Referring now to FIG. 13, an embodiment of a manipulator system 1000 of a computer-assisted surgical system, to which surgical instruments are configured to be mounted for use, is shown. Such a surgical system may further include a user control system, such as a surgeon console (not shown) for receiving input from a user to control instruments coupled to the manipulator system 1000, as well as an auxiliary system, such as auxiliary systems associated with the da Vinci® systems noted above.

As shown in the embodiment of FIG. 13, a manipulator system 1000 includes a base 1020, a main column 1040, and a main boom 1060 connected to main column 1040. Manipulator system 1000 also includes a plurality of manipulator arms 1010, 1011, 1012, 1013, which are each connected to main boom 1060. Manipulator arms 1010, 1011, 1012, 1013 each include an instrument mount portion 1022 to which an instrument 1030 may be mounted, which is illustrated as being attached to manipulator arm 1010. While the manipulator system 1000 of FIG. 13 is shown and described having a main boom 1060 to which the plurality of manipulator arms are coupled and supported thereby, in other embodiments, the plurality of manipulator arms can be coupled and supported by other structures, such as an operating table, a ceiling, wall, or floor of an operating room, etc.

Instrument mount portion 1022 comprises a drive output assembly 1023 and a cannula mount 1024, with a transmission mechanism 1034 (which may generally correspond to the force transmission system 110 discussed in connection with FIG. 1 or 210 discussed in connection with FIG. 2) of the instrument 1030 connecting with the drive output assembly 1023, according to an embodiment. Cannula mount 1024 is configured to hold a cannula 1036 through which a shaft 1032 of instrument 1030 may extend to a surgery site during a surgical procedure. Drive output assembly 1023 contains a variety of drive and other mechanisms that are controlled to respond to input commands at the surgeon console and transmit forces to the transmission mechanism 1034 to actuate the instrument 1030. Although the embodiment of FIG. 13 shows an instrument 1030 attached to only manipulator arm 1010 for ease of viewing, an instrument may be attached to any and each of manipulator arms 1010, 1011, 1012, 1013.

Figure 14:
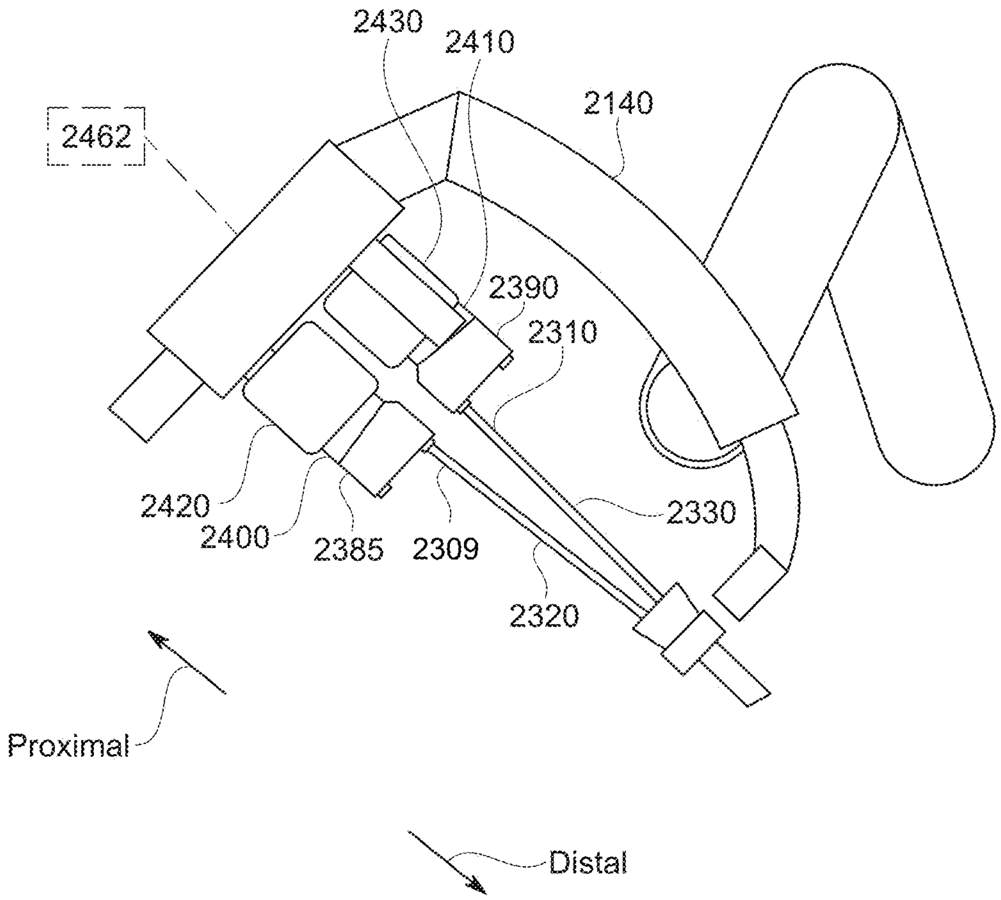
FIG. 14 is a partial schematic view of another embodiment of a manipulator system according to some embodiments of the present disclosure.

Other configurations of surgical systems, such as surgical systems configured for single-port surgery, are also contemplated. For example, with reference now to FIG. 14, a portion of an embodiment of a manipulator arm 2140 of a manipulator system with two surgical instruments 2309, 2310 in an installed position is shown. The surgical instruments 2309, 2310 can generally correspond to instruments discussed above, such as instrument 100 disclosed in connection with FIG. 1. The schematic illustration of FIG. 14 depicts only two surgical instruments for simplicity, but more than two surgical instruments may be mounted in an installed position at a manipulator system as those having ordinary skill in the art are familiar with. Each surgical instrument 2309, 2310 includes a shaft 2320, 2330 that at a distal end has a moveable end effector or an endoscope, camera, or other sensing device, and may or may not include a wrist mechanism (not shown) to control the movement of the distal end.

In the embodiment of FIG. 14, the distal end portions of the surgical instruments 2309, 2310 are received through a single port structure 2380 to be introduced into the patient. As shown, the port structure includes a cannula and an instrument entry guide inserted into the cannula. Individual instruments are inserted into the entry guide to reach a surgical site.

Other configurations of manipulator systems that can be used in conjunction with the present disclosure can use several individual manipulator arms. In addition, individual manipulator arms may include a single instrument or a plurality of instruments. Further, as discussed above, an instrument may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site.

Transmission mechanisms 2385, 2390 (which may generally correspond to force transmission system 110 disclosed in connection with FIG. 1) are disposed at a proximal end of each shaft 2320, 2330 and connect through a sterile adaptor 2400, 2410 with drive assemblies 2420, 2430. Drive assemblies 2420, 2430 contain a variety of internal mechanisms (not shown) that are controlled by a controller (e.g., at a control cart of a surgical system) to respond to input commands at a surgeon side console of a surgical system to transmit forces to the transmission mechanisms 2385, 2390 to actuate surgical instruments 2309, 2310.

The embodiments described herein are not limited to the embodiments of FIG. 13 and FIG. 14, and various other teleoperated, computer-assisted surgical system configurations may be used with the embodiments described herein. The diameter or diameters of an instrument shaft and end effector are generally selected according to the size of the cannula with which the instrument will be used and depending on the surgical procedures being performed.

This description and the accompanying drawings that illustrate various embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to another embodiment, the element may nevertheless be claimed as included in the other embodiment.

For the purposes of this specification and appended claims, unless otherwise indicated, all numbers expressing quantities, percentages, or proportions, and other numerical values used in the specification and claims, are to be understood as being modified in all instances by the term “about,” to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms “a,” “an,” and “the,” and any singular use of any word, include plural referents unless expressly and unequivocally limited to one referent. As used herein, the term “include” and its grammatical variants are intended to be non-limiting, such that recitation of items in a list is not to the exclusion of other like items that can be substituted or added to the listed items.

Further, this description’s terminology is not intended to limit the invention. For example, spatially relative terms—such as “beneath”, “below”, “lower”, “above”, “upper”, “proximal”, “distal”, and the like—may be used to describe one element’s or feature’s relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as “below” or “beneath” other elements or features would then be “above” or “over” the other elements or features. Thus, the exemplary term “below” can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with the following claims being entitled to their fullest breadth, including equivalents, under the applicable law.

What is claimed is:

1. An instrument, comprising:
- a shaft;
- a moveable component coupled to the shaft;
- an actuation member drive assembly coupled to the shaft and comprising:
  - a rotatable drive member,
  - a ring gear operably coupled to the rotatable drive member and configured to rotate in response to rotation of the rotatable drive member, and
  - a planet gear meshed with the ring gear and comprising a bore with internal threads;
- an actuation member extending through the shaft and operably coupled to the moveable component and the planet gear; and
- a lead screw coupled to the actuation member and engaged with the internal threads in the bore of the planet gear,
- wherein the actuation member is moveable in translation in response to rotation of the planet gear.

2. The instrument of claim 1, wherein:
- the planet gear is a first planet gear;
- the actuation member is a first actuation member;
- the first actuation member is movable in translation in a first direction in response to rotation of the first planet gear; and
- the instrument further comprises:
  - a second planet gear meshed with the ring gear, and
  - a second actuation member operably coupled to the moveable component and to the second planet gear,
  - wherein the second actuation member is movable in translation in response to rotation of the second planet gear.

3. The instrument of claim 2, wherein, in response to rotation of the ring gear, the first actuation member is movable in a first direction, and the second actuation member is movable in a second direction, wherein the second direction is opposite the first direction.

4. The instrument of claim 1, wherein the moveable component comprises an articulable component configured to articulate in pitch and yaw.

5. The instrument of claim 1, wherein the moveable component comprises an end effector.

6. An instrument comprising:
- a shaft;
- an articulable component coupled to the shaft and configured to articulate relative to the shaft;

a force transmission system coupled to the shaft and comprising:

a ring gear, a first planet gear meshed with the ring gear, a second planet gear meshed with the ring gear, a first lead screw comprising left-hand screw threading in threaded engagement with the first planet gear, and a second lead screw comprising right-hand screw threading in threaded engagement with the second planet gear;

a first actuation member extending through the shaft and operably coupled to the articulable component and the first lead screw; and a second actuation member extending through the shaft and operably coupled to the articulable component and the second lead screw.

7. The instrument of claim 6, wherein the ring gear is operably coupled to a drive input of the force transmission system by one or more idler gears.

8. The instrument of claim 6, wherein the first planet gear comprises a first planet gear inner member and a first planet gear outer member.

9. The instrument of claim 8, wherein the first planet gear inner member and the first planet gear outer member are rotationally coupled to rotate together.

10. The instrument of claim 9, wherein:

the first planet gear inner member comprises a material having a first ductility;

the first planet gear outer member comprises a material having a second ductility; and the first ductility is less than the second ductility.

11. The instrument of claim 6, wherein the first lead screw comprises features configured to prevent rotation of the first lead screw relative to the shaft.

12. The instrument of claim 6, wherein:

the instrument further comprises:

a roll gear coupled to the shaft to rotate the shaft in response to a roll input received at the force transmission system, and the ring gear, the first planet gear, the second planet gear, the first lead screw, the second lead screw, the first actuation member, and the second actuation member are components of an actuation member drive assembly configured to rotate with the shaft in response to the roll input.

13. The instrument of claim 12, wherein the actuation member drive assembly is removable from the force transmission system.

14. A method of tensioning first and second actuation members coupled to an articulable structure of a medical instrument, the method comprising:

applying a first tensile force to a first actuation member coupled to a first lead screw by driving the first lead screw;

applying a second tensile force to a second actuation member coupled to a second lead screw by driving the second lead screw;

maintaining the first tensile force in the first actuation member by coupling the first lead screw with a first planet gear and meshing the first planet gear to a ring gear; and maintaining the second tensile force in the second actuation member by engaging the second lead screw with a second planet gear and meshing the second planet gear to the ring gear.

15. The method of claim 14, wherein coupling the first lead screw with the first planet gear comprises:

engaging a first planet gear inner member with the first lead screw; and engaging a first planet gear outer member with the first planet gear inner member and with the ring gear.

16. The method of claim 15, wherein engaging the first planet gear outer member with the first planet gear inner member comprises pressing the first planet gear outer member onto the first planet gear inner member.

17. The method of claim 14, wherein applying a first tensile force to a first actuation member coupled to a first lead screw by driving the first lead screw comprises rotating a first planet gear inner member engaged with the first lead screw in a first rotational direction.

18. The method of claim 17, wherein applying a second tensile force to a second actuation member coupled to a second lead screw by driving the second lead screw comprises rotating a second planet gear inner member engaged with the second lead screw in a second rotational direction opposite the first rotational direction.

* * * * *